US008888837B2

(12) United States Patent
Obradović et al.

(10) Patent No.: US 8,888,837 B2
(45) Date of Patent: Nov. 18, 2014

(54) STENT GRAFT

(75) Inventors: Milisav Obradović, Loerrach (DE); Rainer Bregulla, Balingen (DE)

(73) Assignee: Bentley InnoMed GmbH, Hechingen (DE)

( * ) Notice: Subject to any disclaimer, the term of this patent is extended or adjusted under 35 U.S.C. 154(b) by 0 days.

(21) Appl. No.: 13/996,654

(22) PCT Filed: Dec. 20, 2011

(86) PCT No.: PCT/EP2011/006440
§ 371 (c)(1),
(2), (4) Date: Aug. 7, 2013

(87) PCT Pub. No.: WO2012/084202
PCT Pub. Date: Jun. 28, 2012

(65) Prior Publication Data
US 2013/0317595 A1 Nov. 28, 2013

(30) Foreign Application Priority Data
Dec. 22, 2010 (DE) .......................... 10 2010 055 545
Oct. 14, 2011 (DE) .......................... 10 2011 115 902

(51) Int. Cl.
A61F 2/06 (2013.01)
A61F 2/07 (2013.01)
A61F 2/91 (2013.01)
A61F 2/915 (2013.01)

(52) U.S. Cl.
CPC ......... *A61F 2/07* (2013.01); *A61F 2002/91583* (2013.01); *A61F 2002/075* (2013.01); *A61F 2/91* (2013.01); *A61F 2002/91525* (2013.01); *A61F 2/915* (2013.01)

USPC .................. 623/1.13; 623/1.15; 623/1.16

(58) Field of Classification Search
CPC ................ A61F 2/07; A61F 2/82; A61F 2/91
USPC ........................ 623/1.13, 1.15, 1.16
See application file for complete search history.

(56) References Cited

U.S. PATENT DOCUMENTS 6,699,277 B1 * 3/2004 Freidberg et al. ............ 623/1.13

FOREIGN PATENT DOCUMENTS

| EP | 1 266 635 A2 | 12/2002 |
| EP | 1 743 603 A2 | 1/2007 |
| EP | 2 151 217 A1 | 2/2010 |
| WO | WO 01/66035 A2 | 9/2001 |
| WO | WO 2009/035679 A1 | 3/2009 |

OTHER PUBLICATIONS

International Search Report of PCT/EP2011/006440, mailed Jun. 4, 2012.

* cited by examiner

*Primary Examiner* — Jason-Dennis Stewart
(74) *Attorney, Agent, or Firm* — Collard & Roe, P.C.

(57) ABSTRACT

The invention relates to a stent graft comprising a stent (1) having a plurality of ring segments (3) disposed adjacent to one another and connected to one another and at least one membrane (2) having at least one marginal ring segment (4) having a meandering web configuration, wherein web loops (5) which point inwards or outwards are cut in such a way as to produce spring tabs (6) which are disposed so that they engage positively in the web loops (5) and are resiliently movable against the web configuration, wherein the membrane (2) is gripped between the spring tabs (6) and the web.

13 Claims, 4 Drawing Sheets

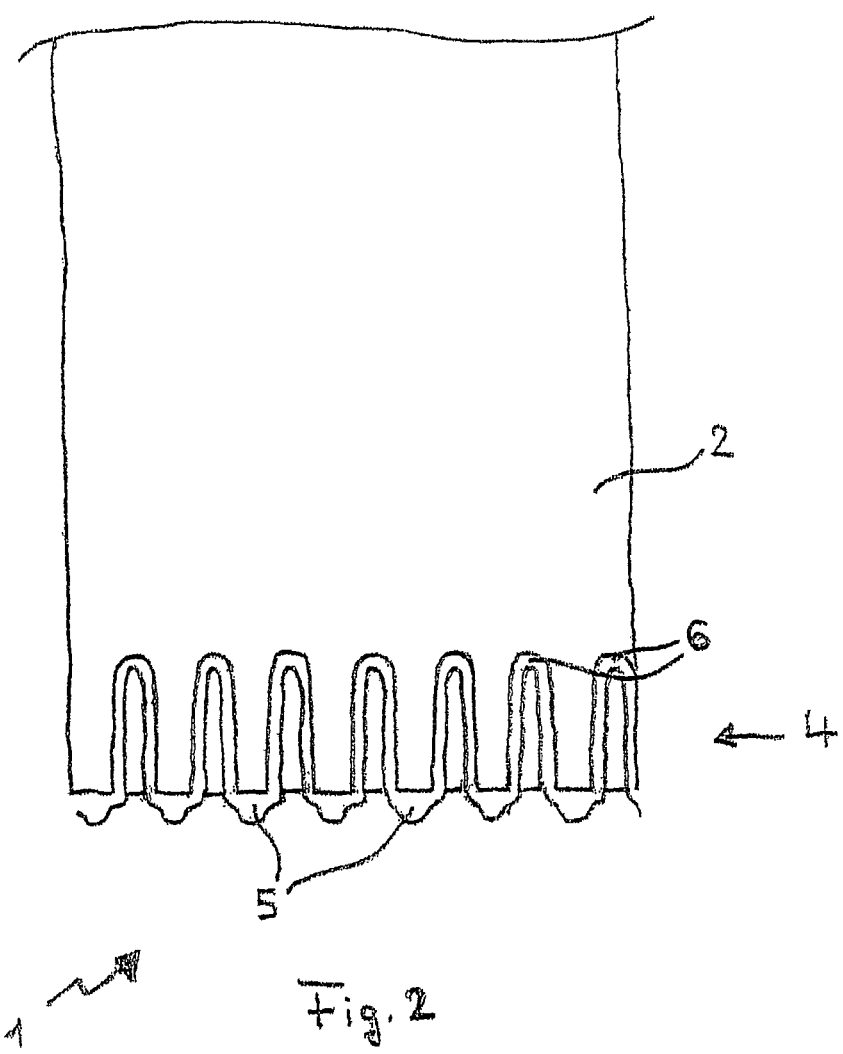

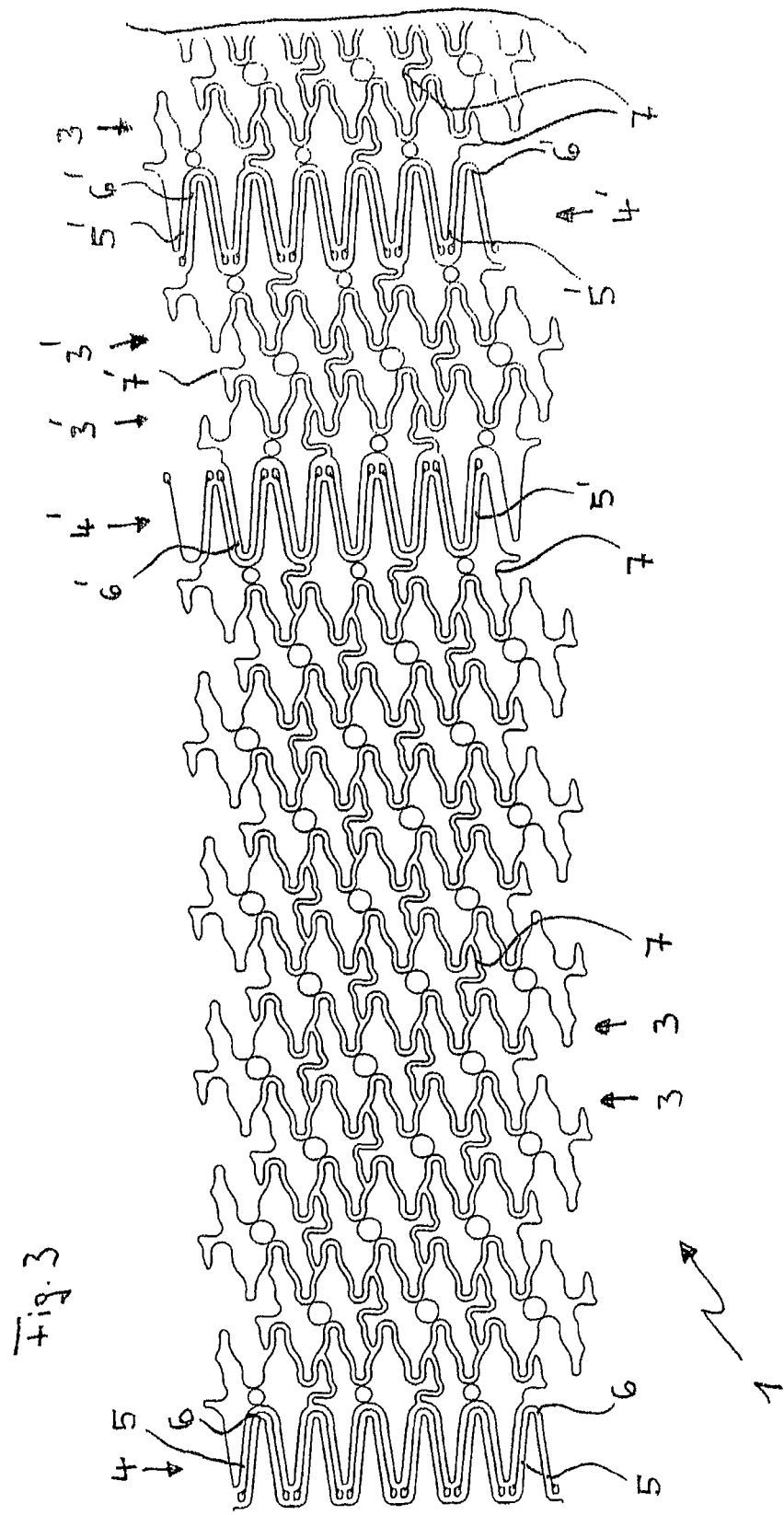

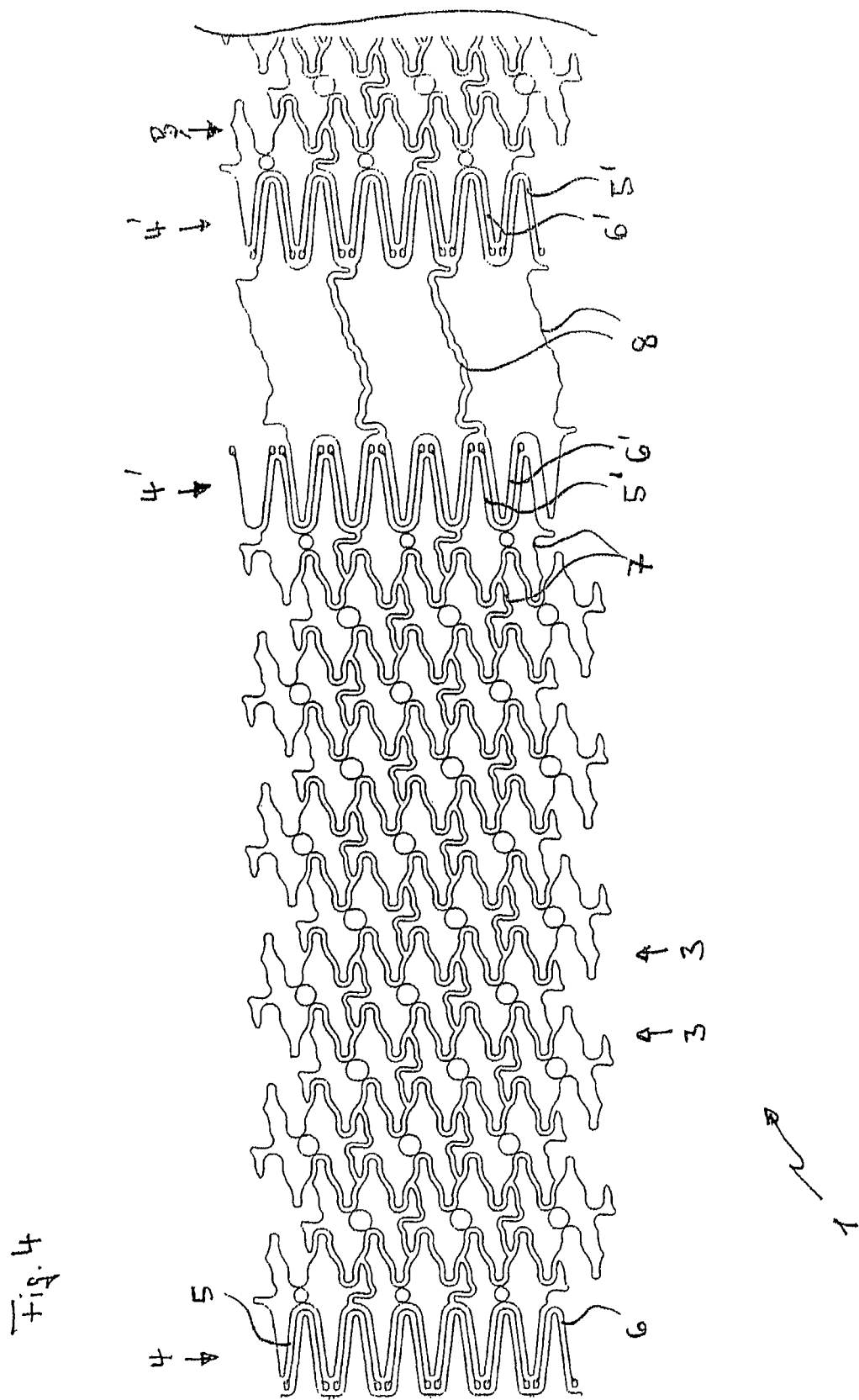

STENT GRAFT

CROSS REFERENCE TO RELATED APPLICATIONS

Figure 1:
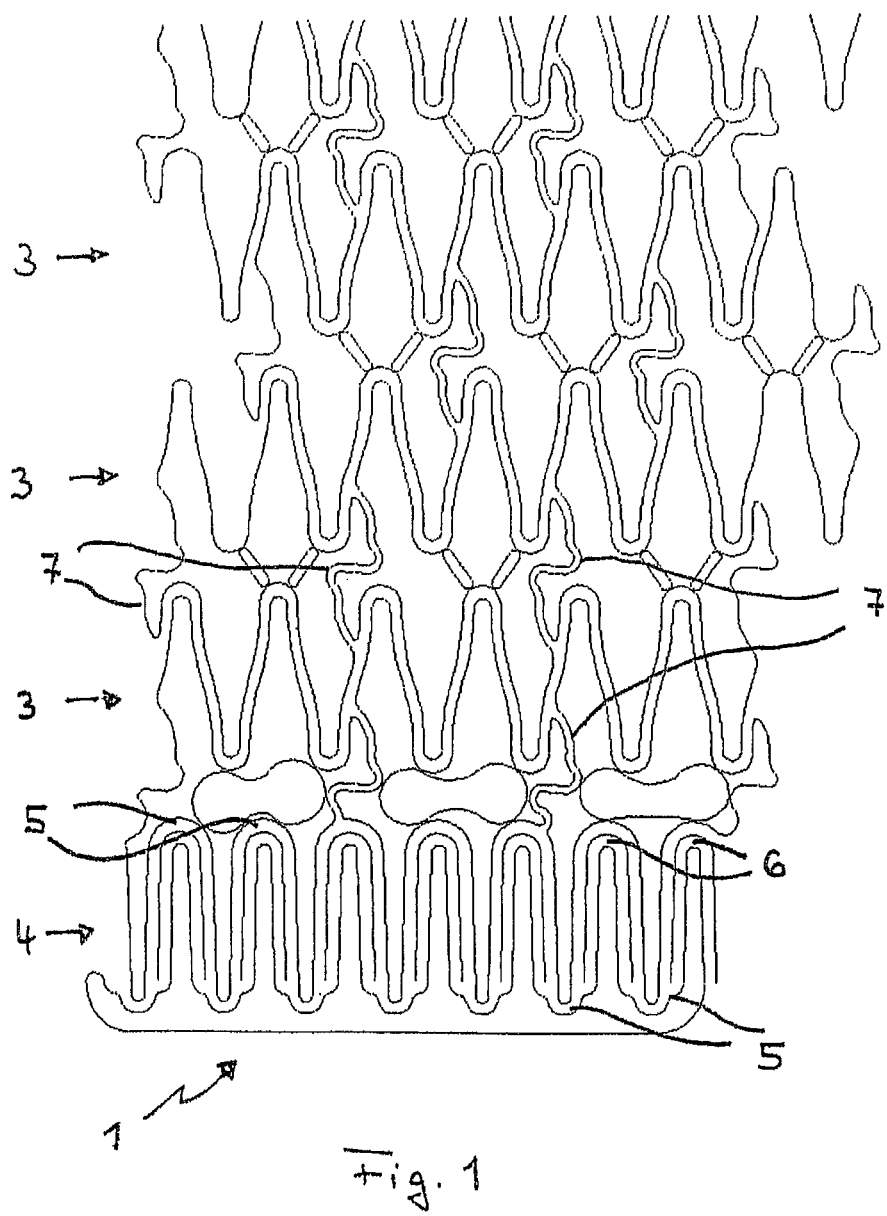

This application is the National Stage of PCT/EP2011/006440 filed on Dec. 20, 2011, which claims priority under 35 U.S.C. §119 German Application No. 10 2010 055 545.2 filed on Dec. 22, 2010 German Application No. 10 2011 115 902.2 filed on Oct. 14, 2011, the disclosures of which are incorporated by reference. The international application under PCT article 21(2) was not published in English.

The invention relates to a stent graft composed of a stent having a plurality of ring segments disposed next to one another and connected with one another and at least one membrane. The invention furthermore relates to the use of such a stent graft for the treatment of vascular malformations.

Stent grafts of this type are used in blood vessels to support abnormally narrowed, widened, or also damaged blood vessels. In this connection, the combination of stent and membrane serves to treat even extensive sections of blood vessels that require treatment, which require a greater length and, above all, also flexibility of the implant. In particular, stent grafts are used in the bridging of vascular malformations, for example to exclude aneurysms from the blood circulation. In general, balloon catheters are used for the implantation of such stent grafts.

In the state of the art, it is known to use stent grafts that consist of two stents and a flexible membrane, for example composed of Teflon, for this purpose. The document EP 2 151 217 A1 describes such a stent graft. The disclosed stent graft consists of an inner stent and an outer stent disposed coaxially around the first, between which stents a flexible, expandable membrane is disposed. The end regions of the stents, with the membrane disposed between them, are welded.

EP 1 266 635 A2 discloses a stent graft that has a cylindrical stent and a cylindrical membrane, which are connected with one another by way of seams or hooks, for example. In addition or alternatively, the connection can be secured by means of a slight overlap of stent and membrane.

WO 2009/035679 A1 discloses a stent graft that has a continuous inner liner composed of polyester or ePTFE. A stent that encloses the inner liner coaxially is disposed in one region of this inner liner. The regions of the inner liner next to the stent are mantled with a second layer of polyester of ePTFE, in order to increase the wall thickness of the implant in the region not supported by the stent. The end regions of stent and second layer are pushed against one another. If necessary, reinforcement material, for example ePTFE, can additionally be applied to the outside of the stent graft components, particularly at the transitions between stent and second layer.

Of the stated stent grafts having a connection of membrane and a stent, only the graft shown in EP 1 266 635 A2 connects precisely one stent with precisely one membrane. The other solutions in the state of the art always require a further stent or a further membrane, which are disposed coaxially about the first stent or the first membrane, respectively, for reinforcement.

The solution according to EP 1 266 635 A2 uses hooks or threads and/or alternatively, an overlap of the two components for the connection between stent and membrane. In this connection, the durability of the hooks and threads is always problematic, because they are exposed to great friction forces within the blood vessel. Likewise, there is a risk of tissue irritation or injury due to projecting hooks or projecting edges between stent and membrane.

It is therefore the task of the present invention to create a stent graft that connects stent and membrane with one another in simple and durable manner, uses up little vascular lumen, and does not cause any tissue irritation or injury.

The invention accomplishes this task with the stent graft of the type indicated initially, having at least one edge-positioned ring segment having a meander-shaped strut progression, on which strut loops that face inward or outward are cut in, in such a manner that spring tongues are formed, which are disposed in the strut loops with shape fit, and can be resiliently moved counter to the strut progression, whereby the membrane is clamped in between spring tongues and strut.

The stent graft according to the invention consists of a plurality of ring segments connected with one another, which are disposed in the center region. These ring segments correspond to the ring segments of conventional stents, as they have been proposed and are in use multiple times. At least one edge-positioned ring segment is configured and modified according to the invention; it has a meander-shaped strut progression, and spring tongues are cut into its strut loops.

Edge-positioned ring segments are understood to be those ring segments that are disposed at the edge of the membrane. In most cases, they will either be disposed in the end position on the stent, in other words delimit the stent at its ends, or are disposed in the immediate vicinity of the end-positioned ring segments. Preferably, they are end-positioned ring segments. In this connection, according to the invention, it is possible that only one of these edge-positioned ring segments is provided with spring tongues, but preferably, edge-positioned ring segments on both stent ends are involved.

A meander-shaped strut progression of the edge-positioned ring segments is understood to mean not only a wave-shaped strut progression but also a zigzag-shaped strut progression. Wave-shaped and zigzag-shaped strut progressions are usual, to a great extent, for vascular stents, in order to at least partially balance out the length contraction that occurs during expansion.

To form the spring tongues, partial cuts are made into the strut loops of the edge-positioned ring segments, so that spring tongues that can move counter to the strut progression are formed. In this connection, cuts can be made either into the strut loops that face inward or those that face outward, so that inward-facing or outward-facing spring tongues are formed. The spring tongues themselves are fitted into the strut loops with shape fit, in the production state of the stent (in other words before it is crimped onto a balloon or before its expansion).

In order to not impair the strut strength as the result of the cuts into the strut loops, it is advisable to increase the strut width in the region of the formation of the spring tongues, for example to double it. This means that the spring tongues have an essentially normal strut width.

Attachment of the membrane, using spring tongues disposed next to one another on the stent, allows simple and secure connection of stent and membrane. The spring tongues disposed in the strut loops are produced by means of laser cutting, for example. Clamping of the membrane under the spring tongues can be easily brought about in terms of production technology. In this connection, integration of the connection elements between stent and membrane into the stent as spring tongues eliminates the risk that connection components come loose from the stent and get into the bloodstream, in freely mobile manner, as can occur in the case of other connection elements.

To produce a uniform connection between stent and membrane, it is practical to dispose a greater number of spring tongues that face in the same direction next to one another. In particular, all of the strut loops of the edge-positioned ring segment, in each instance, that face in the same direction are equipped with a spring tongue. These spring tongues are then oriented parallel to the longitudinal axis of the stent and preferably face stent-inward. In this connection, the shape of the spring tongues corresponds to the shape of the strut loops, to a great extent.

In general, the spring tongues are oriented parallel to the longitudinal axis of the stent. However, deviations from parallelity are also possible, if the cuts and the contact points of the edge segments or strut loops are configured accordingly.

The number of spring tongues of an edge-positioned ring segment is fundamentally based on the desired strength of the connection between stent and membrane, in each instance. In general, at least two opposite strut loops of an edge-positioned ring segment, preferably all the strut loops of the edge-positioned ring segment will be equipped with spring tongues.

The stent graft according to the invention will generally have a stent that can be expanded by means of a balloon catheter and is produced, for example, from a medically acceptable steel.

Alternatively, those variants are also possible, in which the stent is configured to be self-expanding, for example by means of the use of a shape memory alloy such as nitinol.

The membrane, generally a film or a tube, can consist of all materials usual and approved in medical technology. However, PTFE and polyester are particularly suitable. A membrane composed of ePTFE is particularly preferred. In this connection, the membrane can additionally be functionally coated, for example with inflammation-inhibiting, proliferation-inhibiting, or therapeutic substances, for example with rapamycin, paclitaxel or heparin. The membrane is preferably configured in tubular shape and has the required expansion capacity for going along with the stent expansion.

The edge-positioned ring segment(s) with a meander-shaped strut progression and the integrated spring tongues are, in particular, simultaneously the end-positioned ring segments of the stent part of the stent graft according to the invention.

The spring tongues of the edge-positioned ring segments having a meander-shaped strut progression preferably face stent-inward. The membrane clamped between the strut loops and spring tongues can be folded back on itself in order to improve the seat in the end region that comes to lie under the spring tongues, in order to achieve a better clamping effect.

The stent graft according to the invention can have the membrane on the inside or the outside. Placement of the membrane on the outside is preferred. This placement has the advantage that the effect of the stent structure on the vascular wall is alleviated by the membrane that lies in between. In particular, the membrane is clamped in place in the edge-positioned ring segments at both ends of the stent.

Furthermore, a variant is possible, in which the membrane is clamped into the spring tongues lying inside the stent, runs over the stent surface on the outside, and is held by the spring tongues on the inside again, at the opposite end. In this case, the spring tongues preferably face outward.

Preferably, the membrane is additionally fixed in place on edge-positioned ring segments by means of gluing. This can take place by means of a body-compatible adhesive, but preferably by way of an adhesive tape that is glued over the membrane at the level of the spring tongues. Such an adhesive tape also serves, in addition to the securing aspect, to protect the vascular wall from direct contact with the spring tongues of the edge-positioned ring segments.

The stent grafts according to the invention can have the membrane at any desired location, and also can have more than one membrane. For example, the membrane can be disposed only at one or the other end of the stent, or centered in the stent, and can leave stent regions free. Furthermore, it is possible to provide more than just one membrane, which are disposed at the ends, for example, with an interstice that remains free. If more than just one membrane is present, each is fixed in place on the stent structure by itself, by way of corresponding spring tongues and, if necessary, by means of gluing.

If two membranes, for example, are disposed in an end position, the part of the stent graft that lies between them and is not covered by a membrane can be disposed in the region of a vascular junction, so that the blood flow in the branched-off blood vessel is not impaired. For this purpose, the two stent halves that have the membrane can also be only loosely connected with one another by means of what are called connectors. This furthermore brings with it great flexibility in this region.

The stent grafts according to the invention are primarily used for treatment of vascular malformations. This can involve closing off branched-off blood vessels, but also shutting down aneurysms or arteriovenous shunts.

Furthermore, embodiments are possible in which the stent graft according to the invention has two stent units that serve to clamp a tubular membrane that lies between them in place in a blood vessel. In this case, the stent has the clamping connection for fixing the membrane in place only at one end; the other end of the tubular membrane is connected with the second stent. Such a stent graft can be implanted in blood vessels that are damaged over a large area, for example after obliteration of the epithelial cell layer of a blood vessel.

The invention will be described in greater detail in the following, using the figures. These show:

FIG. 1 a stent modified according to the invention,

FIG. 2 a stent graft according to the invention,

FIG. 3 a further stent according to the invention, to be covered with two membranes, and FIG. 4 a stent according to the invention, to be covered with two membranes, and a flexible connection of the two stent parts.

FIG. 1 shows a stent 1 modified according to the invention, as modified for fixing a membrane in place by way of spring tongues 6. The stent 1 consists of a plurality of ring segments 3, which have an essentially zigzag-shaped progression. In the figure, the stent 1 is shown in the cut-open and spread-out state; in the original state after production, it is a tube composed of struts and provided with perforations, for example made of a medical steel or nitinol. Production takes place in known manner, by means of laser cutting of a suitably dimensioned tube.

The ring segments 3 are connected with one another by means of elongation elements 7, in such a manner that when the stent is placed over a balloon, the length reduction that results from the expansion of the ring segments 3 is compensated, at least in part, by stretching of the connection elements 7.

The edge-positioned ring segment 4 at the stent end has a meander-shaped progression. A zigzag-shaped progression would also be possible. The individual struts form strut loops 5 that run over the circumference of the stent in wave shape or meander shape. In this connection, the individual strut loops 5 have incisions 8 in the progression of their tongues that face stent-inward, which incisions cause spring tongues 6 to be formed, which tongues can be resiliently moved counter to the general progression of the struts of the edge-positioned ring segments 4. This makes it possible to push a membrane in between the spring tongues 6 and the strut loops 5, which membrane is held in place there, in clamped manner.

It should be stated that the structure of the stent itself is not decisive for a stent graft according to the invention. The ring segments can have different structures. The important thing is that an edge-positioned ring segment is present, into which spring tongues are cut, in order to fix a membrane in place in them.

FIG. 2 shows a stent graft according to the invention with a stent according to FIG. 1 and a membrane 2 laid in. The end-side strut loops 5 can be seen, as can the spring tongues 6, which come to lie on the membrane 2. In the case of securing of the membrane on the stent with an adhesive, an adhesive tape is glued over the spring tongues 6 for this purpose, once the membrane has been laid down.

FIG. 3 shows a modified stent 1 according to the invention, which is divided into two parts, which can each, by themselves, be covered by membranes. In the left part, the edge-positioned ring segments 4 are equipped with strut loops 5 and spring tongues 6. This is followed by a number of ring segments that are connected with one another by way of connection or elongation elements 7, in each instance. In the central region of the stents, a further "edge-positioned" ring segment 4' having strut loops 5' and spring tongues 6' follows. A transition region with ring segments 3' and elongation elements 7' follows, located in the central region of the stent 1, and these are followed by another "edge-positioned" ring segment 4' having strut loops 5' and spring tongues 6'. Ring segments 3 follow, which are connected by way of elongation elements 7, as does (not shown any longer) the other end of the stent 1, having another edge-positioned ring segment 4 having strut loops 5 and spring tongues 6.

The spring tongues 6 and 6' of the stent half shown on the left side face toward one another in the case shown, and accommodate the tubular membrane between them. The same holds true analogously for the right-side part of the stent 1.

FIG. 4 shows another embodiment of a stent according to the invention, for the production of a stent graft having two membranes. In this case, the stent 1 is also equipped with edge-positioned ring segments 4 at both ends (left-side end is shown), which in turn have strut loops 5 and spring tongues 6. The spring tongues 6 are directed stent-inward. For the remainder, the stent has the usual ring segments 3 that cover the left part of the stent, between the edge-positioned segments 4 and 4', covered by the membrane in the finished stent graft. The individual ring segments 3 and 4 are connected with one another by way of connection elements 7.

Like the edge-positioned ring segments 4, the edge-positioned ring segments 4' disposed centrally also have spring tongues 6' and strut loops 5'.

The right stent half, shown only with the left-side end, corresponds to the left stent half in all points. The two stent halves are coupled with one another by means of connectors 8. In the case shown, the stent 1 has a total of three connectors 8. The connectors leave a greater free space between the two stent halves, which makes it possible, for one thing, to keep descending blood vessels free, but for another thing, brings increased flexibility with it.

Aside from the connectors 8 and the ring segments 3' and connection elements 7', the stent of FIG. 4 corresponds to that of FIG. 3 in all other points.

The stent graft according to the invention is crimped onto a balloon catheter in usual manner, and expanded at the location of use, using the usual technique. In this connection, the stent 1, with the membrane 2, comes to lie against the vascular wall. The membrane 2 is situated between stent 1 and vascular wall.

The invention claimed is:

1. Stent graft composed of a stent (1) having a plurality of ring segments (3) disposed next to one another and connected with one another and at least one membrane (2), comprising at least one edge-positioned ring segment (4) having a meander-shaped strut progression, on which strut loops (5) that face inward or outward are cut in such a manner that spring tongues (6) are formed, which are disposed in the strut loops (5) with shape fit, and can be resiliently moved counter to the strut progression, wherein the membrane is clamped in between the spring tongues (6) and the strut loops.

2. Stent graft according to claim 1, wherein at least one edge-positioned ring segment (4) is disposed to be end-positioned.

3. Stent graft according to claim 1, wherein the spring tongues (6) point stent-inward.

4. Stent graft according to claim 1, wherein the stent (1) has a membrane (2) in the form of a tube.

5. Stent graft according to claim 4, wherein the membrane (2) surrounds the stent (1).

6. Stent graft according to claim 1, wherein the membrane (2) is secured in the spring tongues (6) by means of gluing, preferably using adhesive tape.

7. Stent graft according to claim 1, further comprising multiple membranes (2) disposed in certain sections, which are secured on spring tongues (6), in each instance.

8. Stent graft according to claim 1, wherein the edge region of the membrane (2) clamped into the spring tongues (6) is folded over.

9. Stent graft according to claim 1, wherein the membrane (2) comprises an ePTFE tube.

10. Stent graft according to claim 1, wherein the stent (1) is a balloon-expandable stent.

11. Stent graft according to claim 10, wherein the stent is crimped onto the balloon of a balloon catheter.

12. Stent graft according to claim 1, having a self-expanding stent composed of a shape memory alloy, particularly nitinol.

13. Use of a stent graft according to claim 1 for the treatment of vascular malformations.

* * * * *